United States Patent
Pruss et al.

(10) Patent No.: US 7,985,774 B2
(45) Date of Patent: Jul. 26, 2011

(54) USE OF 3,5-SECO-4-NOR-CHOLESTANE DERIVATIVES FOR OBTAINING A CYTOPROTECTIVE DRUG

(75) Inventors: Rebecca Pruss, Cassis (FR); Bruno Buisson, Marseilles (FR); Thierry Bordet, Marseilles (FR)

(73) Assignee: Trophos, Marseilles Cedex (FR)

(*) Notice: Subject to any disclaimer, the term of this patent is extended or adjusted under 35 U.S.C. 154(b) by 256 days.

(21) Appl. No.: 12/282,249

(22) PCT Filed: Feb. 23, 2007

(86) PCT No.: PCT/FR2007/000330
§ 371 (c)(1),
(2), (4) Date: Nov. 6, 2008

(87) PCT Pub. No.: WO2007/101925
PCT Pub. Date: Sep. 13, 2007

(65) Prior Publication Data
US 2009/0312434 A1    Dec. 17, 2009

(30) Foreign Application Priority Data

Mar. 9, 2006  (FR) ..................................... 06 02091

(51) Int. Cl.
*A61K 31/15* (2006.01)
*A61K 31/12* (2006.01)
(52) U.S. Cl. ...................................... 514/640; 514/675
(58) Field of Classification Search .................. 514/640, 514/675
See application file for complete search history.

(56) References Cited

U.S. PATENT DOCUMENTS
3,763,228 A    10/1973    Pettit et al.

FOREIGN PATENT DOCUMENTS

| EP | 0 572 165 A1 | * | 1/1993 |
| WO | WO 2004/106370 | | 12/2004 |
| WO | WO 2005/007192 | | 1/2005 |
| WO | WO 2006/027454 | | 3/2006 |

OTHER PUBLICATIONS

Smith et al., "Steroid lysis of protoplasts and effects of stabilizers and steroid antagonists", Applied Microbiology, 13(5), 706-12, 1965.*
Smith et al., "Relation of Surfactant Properties of Some Synthetic Steroids to Bactericidal Action", Journal of Pharmaceutical Sciences, American Pharmaceutical Association, Wash., DC, US, vol. 54, No. 10 (1964), pp. 1214-1216.*
Lingham R.B., et al., "Clavaric Acid and Steroidal Analogues as ras- and FFP-directed inhibitors of human farnesyl-protein transferase", Journal of Medicinal Chemistry, American Chemical Society, Wash. DC, US, vol. 41, No. 23, (1998), pp. 4492-4501.*
Peng H. et al., "Steroidal Derived Acids as Inhibitors of Human Cdc25A Protein Phosphatase.", Bioorganic & Medicinal Chemistry, FEB, (2000), vol. 8, No. 2, pp. 299-306.*
Edward, et al., "Ring-Chain Tautomerism of 5-Oxo-3,5-seco-A-norcholestan-3-ol", *Canadian Journal of Chemistry*, vol. 51, pp. 1610-1616, 1973.
Rodewald, et al., "Aza-steroid Alkaloids. Synthesis of A-Nor-B-homo-5-azacholestane", *Bulletin De L'Academie Polonaie Des Sciences*, vol. XI, No. 8, pp. 437-441, 1963.
Smith, et al., "Effects of Protein, Lipids, and Surfactants on the Antimicrobial Activity of Synthetic Steroids", *Applied Microbiology*, vol. 11, pp. 542-544, Nov. 1963.

* cited by examiner

*Primary Examiner* — Raymond Henley, III
(74) *Attorney, Agent, or Firm* — Browdy and Neimark, PLLC; Iver P. Cooper

(57) ABSTRACT

The present invention relates to the use of 3,5-seco-4-nor-cholestane derivatives for obtaining a cytoprotective drug, with the exception of a neuroprotective drug, notably a cardioprotective or hepatoprotective drug.

13 Claims, No Drawings

USE OF 3,5-SECO-4-NOR-CHOLESTANE DERIVATIVES FOR OBTAINING A CYTOPROTECTIVE DRUG

The present invention relates to the use of 3,5-seco-4-nor-cholestane derivatives for obtaining a cytoprotective drug, with the exception of a neuroprotective drug.

Cellular degenerative processes are characterized by dysfunction of cells often causing undesirable cell activities and cell death.

The cells have developed adaptation mechanisms in reaction to stress, which extend their lifetime or delay or prevent cell death (cytoprotective mechanisms).

However, these cytoprotective mechanisms are sometimes insufficient, inadequate or induced too late to be efficient and the cells die. It may therefore prove to be of interest to have novel cytoprotective drugs, which would promote cytoprotection. This is one of the objects of the present invention.

The term <<cytoprotective>> makes reference to the capability of either natural agents or not of protecting a cell against cell death, particularly pathological cell death, and/or against cell dysfunctions leading to cell death. These cell dysfunctions may for example be of mitochondrial origin such as a reduction in the capability of generating ATP, an incapability of capturing and/or retaining calcium, or the generation of free radicals.

Among the main mechanisms of cell death, a distinction is essentially made between necrosis, apoptosis, and necroptosis.

Necrosis is a so-called "accidental" cell death which occurs during damage to tissue. It is the plasmic membrane of the cell which is affected the most, causing modification of the homeostasis of the cell. The cells will soak up water to the extent that this will cause lysis of their plasmic membrane. This cell lysis leads to release of the cytoplasm contents into the surrounding medium. Necrosis is at the origin of the inflammatory process.

Necrosis may affect a set of cells or a tissue while other neighboring portions remain alive. The resulting transformation is mortification of the cells or of the tissues.

In other words, necrosis is defined by morphological modifications which occur when a cell reaches the end of its life as a result of events such as a significant trauma such as interruption or reduction of the blood supply at an organ, hyperthermia (significant rise in temperature), intoxication by a chemical, a physical shock, etc. One of the most known necroses is that of the myocardium during infarction (interruption of the blood stream supply at the cardiac muscle) due to occlusion (obstruction) of a coronary artery.

Apoptosis is an integral part of the normal physiology of an organism. It is a highly regulated physiological form of cell death and it is required for the survival of multicellular organisms. Apoptosis is a process which plays a primordial role during embryogenesis.

Cells in apoptosis or apoptotic cells will isolate themselves from the other cells. Apoptosis usually involves individual cells in a tissue and does not cause inflammation. One of the characteristic morphological points of apoptosis is the significant condensation of both the nucleus and cytoplasm which induces significant reduction in the cell volume. The nucleus then fragments, each fragment are surrounded by a dual envelope. Apoptotic bodies (cytoplasmic and nuclear elements) are then released and will be absorbed through phagocytosis by neighboring cells.

Apoptosis may be induced in different ways. For instance, radiation, the presence of a chemical or hormone, are stimuli which may induce a cascade of apoptotic events in the cell. Intracellular signals such as incomplete mitosis or DNA damage may also induce apoptosis.

Apoptosis also occurs after the action of a genotoxic agent or during a disease. Certain pathologies are characterized by abnormal apoptosis, causing the loss of certain cell populations, as for example hepatotoxicity, retinopathies, cardiotoxicity.

A distinction is therefore made between physiological apoptosis and pathological apoptosis. The invention is essentially focused on pathological apoptosis.

There exist other mechanisms of cell death, such as for example necroptosis, which has characteristics of necrosis and apoptosis. A cell which is dying by necroptosis has similar characteristics to those of a cell dying by necrosis, but the biochemical steps of this mechanism are more similar to those of apoptosis. This mechanism of cell death for example occurs in ischemia.

Accordingly, one of the objects of the present invention is also to make novel drugs available with which it may be possible to prevent and/or treat necrosis and/or pathological apoptosis and/or necroptosis (anti-necrotic and/or anti-apoptotic and/or anti-necroptotic drugs).

Cell degenerative processes may inter alia result from pathological situations grouped under the term of degenerative diseases or affections, traumas or of exposure to various factors.

These traumas and factors may for example include exposure to radiations (UV, gamma radiations), hypoxia or lack of oxygen, lack of nutrients, lack of growth factors, poisons, cell toxins, waste, environmental toxins, free radicals, reactive oxygen or even certain medical events and/or procedures such as for example surgical traumas including transplantations of cells, tissues and organs. Chemical or biological agents may also be mentioned, used as therapeutic agents within the context of medical treatments such as for example cytostatic agents or anti-inflammatory agents.

The object of the invention is not to treat extracellular causes of pathologies or degenerative processes which may result in cell death, but actually the consequences at the cell level of said pathological processes or of said pathologies and particularly to protect the cell against said consequences.

Among the most significant pathological situations characterized by a degenerative process, other than neurological or neurodegenerative disorders to which the present invention is not directed the following situations are found:

diseases of the bones, joints, connective tissue and of cartilage, such as osteoporosis, osteomyelitis, arthritises including for example osteoarthritis, rheumatoid arthritis and psoriatic arthritis, avascular necrosis, progressive fibrodysplasia ossificans, rickets, Cushing's syndrome;

muscular diseases such as muscular dystrophy, such as for example Duchenne's muscular dystrophy, myotonic dystrophies, myopathies and myasthenias;

diseases of the skin, such as dermatitis, eczema, psoriasis, aging or even alterations of scarring;

cardiovascular diseases such as cardiac and/or vascular ischemia, myocardium infarction, ischemic cardiopathy, chronic or acute congestive heart failure, cardiac dysrythmia, atrial fibrillation, ventricular fibrillation, paroxystic tachycardia, congestive heart failure, hypertrophic cardiopathy, anoxia, hypoxia, secondary effects due to therapies with anti-cancer agents;

circulatory diseases such as atherosclerosis, arterial scleroses and peripheral vascular diseases, cerebrovascular strokes, aneurisms;

haematological and vascular diseases such as: anemia, vascular amyloidosis, haemorrhages, drepanocytosis, red cell fragmentation syndrome, neutropenia, leukopenia, medullar aplasia, pantocytopenia, thrombocytopenia, haemophilia;

lung diseases including pneumonia, asthma; obstructive chronic diseases of the lungs such as for example chronic bronchitis and emphysema;

diseases of the gastro-intestinal tract, such as ulcers;

diseases of the liver such as for example hepatitis particularly hepatitis of viral origin or having as causative agent other infectious agents, auto-immune hepatitis, fulminating hepatitis, certain hereditary metabolic disorders, Wilson's disease, cirrhoses, non-alcoholic hepatic steatosis, diseases of the liver due to toxins and to drugs;

diseases of the pancreas such as for example acute or chronic pancreatitis;

metabolic diseases such as diabetes mellitus and insipid diabetes, thyroiditisthyroiditis;

diseases of the kidneys such as for example acute renal disorders or glomerulonephritis;

viral and bacterial infections such as septicemia;

severe intoxications by chemicals, toxins or drugs;

degenerative diseases associated with the Acquired Immune Deficiency Syndrome (AIDS);

disorders associated with aging such as the syndrome of accelerated aging;

inflammatory diseases such as Crohn's disease, rheumatoid polyarthritis;

auto-immune diseases such as erythematous lupus;

dental disorders such as those resulting in degradation of tissues such as for example periodontitis;

ophthalmic diseases or disorders including diabetic retinopathies, glaucoma, macular degenerations, retinal degeneration, retinitis pigmentosa, retinal holes or tears, retinal detachment, retinal ischemia, acute retinopathies associated with trauma, inflammatory degenerations, post-surgical complications, medicinal retinopathies, cataract;

disorders of the audition tracts, such as otosclerosis and deafness induced by antibiotics;

diseases associated with mitochondria (mitochondrial pathologies), such as Friedrich's ataxia, congenital muscular dystrophy with structural mitochondrial abnormality, certain myopathies (MELAS syndrome, MERFF syndrome, Pearson's syndrome), MIDD (mitochondrial diabetes and deafness) syndrome, Wolfram's syndrome, dystonia.

The invention is also interested in protecting cells, tissues and/or transplanted organs, whether before, during (removal, transport and/or re-implantation) or after transplantation.

Pharmacologically active compounds are still sought for controlling the degenerative processes mentioned above.

The present invention meets this demand for cytoprotective compounds. Indeed, the Applicant has discovered that 3,5-seco-4-nor-cholestane derivatives, and notably 3,5-seco-4-nor-cholestan-5-one oxime-3-ol and one of its esters are provided with remarkable cytoprotective properties.

This is why the object of the present invention is the use of at least one compound fitting formula I

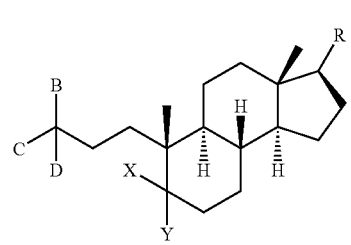

wherein
X and Y taken together represent a ketone function (=O), an oxime group (=NOH) or a methyloxime group (=NHOMe) or X represents a hydroxyl and Y a hydrogen atom, B represents a hydroxyl radical and C and D, either identical or different, represent a hydrogen atom, or a linear or branched alkyl radical comprising 1 to 4 carbon atoms, or B and C taken together represent a ketone function and D a methyl, hydroxyl, or methylamine radical, or B and C represent a hydrogen atom and D a methylamine radical, or B and C taken together represent an oxime group and D a methyl radical, and R represents a linear or branched alkyl radical comprising 1 to 10 carbon atoms, or one of its addition salts with pharmaceutically acceptable acids, or one of its esters or one of the addition salts with pharmaceutically acceptable acids of said esters, for preparing a cytoprotective drug, with the exception of a neuroprotective drug.

According to the invention, the addition salts with pharmaceutically acceptable acids may for example be salts formed with hydrochloric, hydrobromic, nitric, sulfuric, phosphoric, acetic, formic, propionic, benzoic, maleic, fumaric, succinic, tartaric, citric, oxalic, glyoxylic, aspartic, alkane-sulfonic acids such as methane- or ethane-sulfonic acids, aryl-sulfonic acids, such as benzene- or paratoluene-sulfonic acids or carboxylic acids.

According to the invention, the oxime group represents pure or mixed syn and anti isomers, associated with the orientation of the N—O bond, relatively to the double bond C=N.

The radical R of the compounds of formula I which may be used is preferentially the cholestane radical of formula II

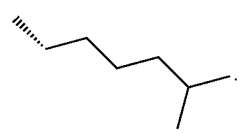

According to other particular embodiments of the invention, the compounds of formula I for which X and Y taken together represent a ketone function, or represent an oxime group, are preferentially used.

According to still other particular embodiments of the invention, the compounds of formula I for which B represents a hydroxyl radical and C and D, either identical or different, represent a hydrogen atom of a linear or branched alkyl radical comprising from 1 to 4 carbon atoms, or further for which B and C taken together represent a ketone function and D represents a methyl radical, are preferentially used.

Most preferentially, at least one compound of formula I is used according to the invention selected from 3,5-seco-4-nor-cholestan-5-one oxime-3-ol, 3,5-seco-4-nor-cholestan-5-one oxime-3-methyl alcohol, or 3,5-seco-4-nor-cholestan-5-one oxime-3-dimethyl alcohol, or one of its addition salts with pharmaceutically acceptable acids, or one of its esters or one of the addition salts with pharmaceutically acceptable acids of said esters.

The interesting cytoprotective properties of compounds of formula I justify their use for preparing a cytoprotective drug, particularly intended for treating or preventing necrosis, and/or pathological apoptosis, and/or necroptosis (anti-necrotic and/or anti-apoptotic and/or anti-necroptotic drugs) or further diseases such as diseases of the bones, joints, connective tissue and cartilage, muscular diseases, skin diseases, cardiovascular diseases, circulatory diseases, hematological and vascular diseases, diseases of the lung, diseases of the gastro-intestinal tract, diseases of the liver, diseases of the pancreas, metabolic diseases, diseases of the kidneys, viral and bacterial infections severe intoxications, degenerative diseases associated with the Acquired Immune Deficiency Syndrome (AIDS), disorders associated with aging, inflammatory diseases, auto-immune diseases, dental disorders, ophthalmic diseases or disorders, diseases of the audition tracts, diseases associated with mitochondria (mitochondrial pathologies).

The invention is also interested in protecting cells, tissues or transplanted organs, whether before, during (removal, transport and/or re-implantation) or after transplantation.

Advantageously, the compounds of formula I may be used in preparing a drug intended for protecting cardiac cells (cardioprotective drug), protecting hepatic cells (hepatoprotective drug) or a drug intended for treating or preventing diseases associated with mitochondria.

According to the invention, the compound of formula I is advantageously present in the cytoprotective drug at physiologically effective doses; said drugs notably contain an effective cytoprotective dose of at least one of the compounds of formula I.

As drugs, the compounds fitting formula I, their esters, their addition salts with pharmaceutically acceptable acids as well as the addition salts with pharmaceutically acceptable acids of said esters, may be formulated for the digestive or parenteral route.

The drugs according to the invention may further comprise at least one other therapeutically active ingredient, whether it is active on the same pathology, or on a different pathology, for simultaneous, separate use or use spread out in time, notably when treating a subject affected by one of the pathologies mentioned earlier.

According to the invention, the compound of formula I may be used in the drug, mixed with one or more inert i.e. pharmaceutically inactive and non-toxic, excipients or carriers. Mention may for example be made of saline, physiological, isotonic, buffered, solutions, etc., compatible with pharmaceutical use and known to one skilled in the art. The compositions may contain one or more agents or carriers selected from dispersants, solubilizers, stabilizers, preservatives, etc. Agents or carriers which may be used in formulations (liquid and/or injectable, and/or solid formulations) are notably methylcellulose, hydroxymethylcellulose, carboxymethylcellulose, cyclodextrins, polysorbate 80, mannitol, gelatin, lactose, vegetable or animal oils, acacia, etc. Preferentially, vegetable oils are used. The compositions may be formulated as an injectable suspension, gels, oils, tablets, suppositories, powders, gelatin capsules, capsules, etc., possibly by means of galenic forms or devices providing prolonged and/or delayed release. For this type of formulation, an agent such as cellulose, carbonates or starches, is used advantageously.

Administration may be performed by any method known to one skilled in the art, preferably orally or by injection, typically via an intraperitoneal, intracerebral, intrathecal, intravenous, intra-arterial or intramuscular route. Oral administration is preferred. If this is a long term treatment, the preferred administration route will be sublingual, oral or transcutaneous.

For injections, the compounds are generally packaged as liquid suspensions, which may be injected by means of syringes or perfusions, for example. It is understood that the flow rate and/or the injected dose or generally the dose to be administered, may be adapted by one skilled in the art depending on the patient, on the pathology, on the administration method, etc. It is understood that repeated administrations may be performed, possibly in combination with other active ingredients or any pharmaceutically acceptable carrier (buffers, saline, isotonic solutions, in the presence of stabilizers, etc.).

The invention may be used in mammals, notably in humans.

Generally, the daily dose of the compound will be the minimum dose for obtaining the desired therapeutic effect The dosages of the compounds described above and for example, of 3,5-seco-4-nor-cholestan-5-one oxime-3-ol will generally be comprised between 0.001 to 100 mg per kilogram daily for humans.

If required, the daily dose may be administrated in two, three, four, five, six or more takings per day or with multiple sub-doses administered at suitable intervals during the day.

The selected amount will depend on multiple factors, in particular on the administration route, on the administration duration, on the moment of administration, on the elimination rate of the compound, on the different product(s) used in combination with the compound, on the age, on the weight and on the physical condition of the patient, as well as on his/her medical history and on any other information known in medicine.

The prescription of the attending physician may begin with dosages less than those generally used, and these dosages will then be gradually increased in order to better control the occurrence of possible secondary effects.

The compositions according to the invention, notably pharmaceutical compositions or drugs, may comprise at least one compound of formula I as described earlier, or on of its addition salts with pharmaceutically acceptable acids or one of its esters or one of the addition salts with pharmaceutically acceptable acids of said esters.

The pharmaceutical compositions according to the invention may further comprise at least one other therapeutically active ingredient, for simultaneous, separate use, or spread over time, notably upon treating a subject affected with one of the pathologies mentioned earlier.

The pharmaceutical compositions according to the invention may advantageously comprise one or more inert, i.e. pharmaceutically inactive and non-toxic, excipients or carriers.

The compounds of formula I

The compounds of formula I used according to the invention may be synthesized by reacting a compound of formula III

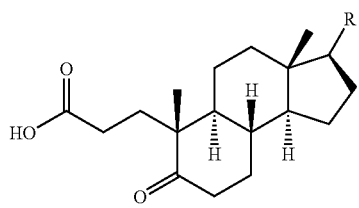

(III)

wherein R has the meanings indicated earlier, which is submitted either to the action of methylamine and then hydroxylamine in order to obtain a compound of formula I wherein R has the meanings indicated earlier, X and Y represent together an oxime group, B represents together with C a ketone function and D a methylamine group or to methylation in order to obtain a compound of formula IV

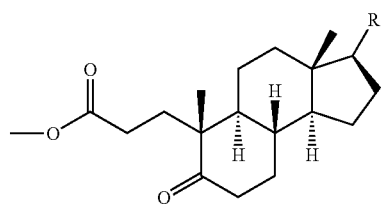

(IV)

wherein R has the meanings indicated earlier, which is submitted to the action of an agent protecting the ketone function in position 5 in order to obtain a compound of formula V

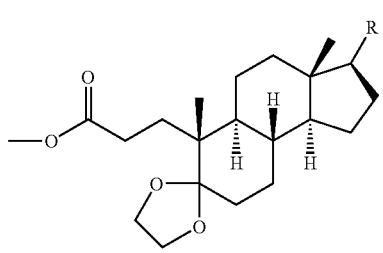

(V)

wherein R has the meanings indicated earlier, which is either reacted with methyl lithium and then is submitted to the action of an agent for de-protecting the ketone function in position 5 and then is reacted with hydroxylamine in order to obtain a compound of formula I wherein R has the meanings indicated earlier, X and Y represent together an oxime group, B represents a hydroxyl group and C and D represent linear or branched alkyl radicals with 1 to 4 carbon atoms, or saponified, and then reacted with a compound of formula $H_3C-NH-OCH_3$, and then reacted with methyl lithium in order to obtain a compound of formula VI

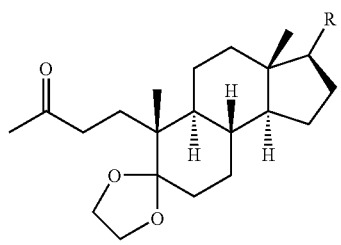

(VI)

which is submitted to reduction of the ketone function and is then submitted to the action of an agent for de-protecting the ketone function in position 5, and then is reacted with hydroxylamine in order to obtain a compound of formula I wherein R has the meanings indicated earlier, X and Y represent together an oxime group, B represents a hydroxyl group and C represents an optionally substituted, linear or branched alkyl radical with 1 to 4 carbon atoms, and D represents a hydrogen atom, or else is reduced in order to obtain a compound of formula VII

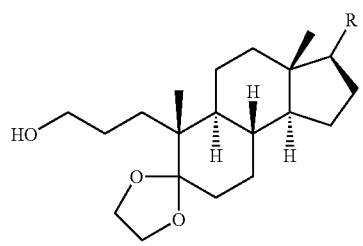

(VII)

wherein R has the meanings indicated earlier, B represents a hydroxyl group and C and D represent a hydrogen atom, which is either submitted to the action of an oxidation agent in order to obtain a compound of formula VIII

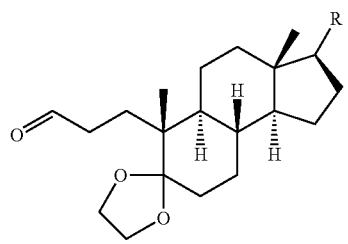

(VIII)

wherein R has the meanings indicated earlier, the Schiff base of which is prepared and then reduced, and is then submitted to the action of an agent for de-protecting the ketone function in position 5, and is then reacted with hydroxylamine in order to obtain a compound of formula I wherein R has the meanings indicated earlier, X and Y represent together an oxime group, B represents a methylamine group, and C and D represent a hydrogen atom, or submitted to the action of an agent for de-protecting the ketone function in position 5, and then reacted with an amine selected from hydroxylamine, methylhydroxylamine and carboxymethylhydroxylamine in order to obtain a compound of formula I wherein R has the meanings indicated earlier, X and Y represent together an oxime, methyloxime and carboxymethyloxime group, respectively, B represents a hydroxyl group and C an D represent a hydrogen atom, and the compounds of formula I are isolated and if desired, salified or esterified, isolated and then if desired, salified.

Under preferential conditions for applying the method described above, the reaction of the compound of formula III with methylamine is conducted in the presence of a coupling agent activating the acid function such as BOP (benzotriazol-1-yl-oxy-tris-(dimethylamino)-phosphonium hexafluorophosphate) or TBTU (2-(1H-benzotriazol-1-yl)-1,1,3,3-tetramethyluronium tetrafluoroborate) advantageously in the presence of a base such as N-methylmorpholine, notably in a suitable solvent such as dichloromethane or dimethylformamide. Preferably it is conducted in the presence of EDCI (1-ethyl-3-(3'-dimethyl-aminopropyl)carbodiimide) associated with 4-dimethylaminopyridine in dichloromethane, the mixture being submitted to stirring at room temperature for 24 hrs. The product is then placed in solution preferably in pyridine, and then 5 to 7 and notably 6 equivalents of hydroxylamine hydrochloride are added.

the methylation of the compound of formula III is achieved by reaction with methanol in the presence of thionyl chloride, preferably by solubilizing the acid of formula II in a suitable volume of a mixture of 70% methanol and 30% dichloromethane. After cooling to 0° C., 3 equivalents of thionyl chloride are added dropwise. Stirring is then performed for 2 hrs at room temperature. On this compound, the protection of the ketone function is preferably carried out by solubilizing the product in an excess, for example 10 equivalents of trimethyl orthoformate and a sufficient volume of ethylene glycol, and then by adding anhydrous p-toluene-sulfonic acid.

the reaction of the compound of formula V with methyl lithium is preferably conducted in anhydrous THF and then after cooling to about −45° C., by adding dropwise an excess of methyl lithium. De-protection of the dioxolane which blocks the ketone function in position 5, is achieved in acetone in the presence of sulphuric acid. Preferably, this is carried out in dioxane, in presence of a mixture of 1/1 water/acetic acid mixture. The oxime of the ketone is advantageously made as above.

the saponification of the compound of formula V is achieved with soda preferably in dioxane. About 2 equivalents of an aqueous soda solution are notably added. This product is reacted with a compound of formula $H_3C—NH—OCH_3$, for example in the presence of a coupling agent activating the acid function such as BOP or TBTU in the presence of a base such as N-methylmorpholine in a suitable solvent such as dichloromethane or dimethylformamide. Preferably, this is conducted in the presence of EDCI associated with hydroxybenzotriazole with triethylamine being added dropwise into the solvent. This product is reacted with methyl lithium under an argon atmosphere according to the procedure described above, and the ketone function in 3 is then reduced by sodium borohydride. The obtained product is then submitted to de-protection of the ketone function in position 5 and reacted with hydroxylamine according to the same procedure as described above.

the reduction of the compound of formula V in order to obtain the compound of formula VII is preferably achieved with lithium aluminum hydride, notably by placing it in suspension in tetrahydrofurane. It is hydrolyzed with precaution by adding a sodium sulfate solution.

the oxidization of the compound of formula VII is achieved by means of pyridinium chlorochromate. On this product, the Schiff base is obtained, which is instantaneously reduced notably by solubilization under argon preferably in ethanol, in the presence of triethylamine, of methylamine hydrochloride and titanium tetra-isopropoxide, and then by adding sodium borohydride. De-protection of the ketone function in position 5 as well as the reaction with hydroxylamine is carried out under the conditions described earlier.

The following examples illustrate the present application without however limiting it.

EXAMPLES

The retention times hereafter are expressed in minutes and hundredths of a minute.

The liquid chromatography method used for the whole of the products is the following:

Column: Macherey-Nagel—Nucleosil® 300-6 C4—150× 4.6 mm Gradient: water(+0.05% of trifluoroacetic acid)/acetonitrile(+0.05% of trifluoroacetic acid)

t=0 min: 60% acetonitrile, 40% $H_2O$
t=6 min: 100% acetonitrile, 0% $H_2O$
t=11 min: 100% acetonitrile, 0% $H_2O$
t=13 min: 60% acetonitrile, 40% $H_2O$
t=15 min: 60% acetonitrile, 40% $H_2O$.

The ionization conditions for the mass spectrometer are:
Temperature of the source: 250° C.
Cone voltage: 50 V
Capillary voltage: 3 kV
Rf lens: 0.3 V Example 1

Synthesis of 3,5-seco-4-nor-cholestane-5-one oxime-3-methylamide

Step A: In a first phase, 250 mg of 3,5-seco-4-nor-cholestane-5-one oxime-3-oic acid, 38 mg of methylamine hydrochloride, 250 mg of EDCI, 100 mg of DMAP and 2.5 mL of dichloromethane are introduced into a flask. The solution is stirred for 24 hours at room temperature and the reaction medium is then diluted by adding dichloromethane and washed with a 10% sodium bicarbonate solution. The organic phase is dried on magnesium sulfate and then concentrated under reduced pressure. The obtained residue is purified by flash chromatography ($CH_2Cl_2$/MeOH 95/5). 176 mg of 3,5-seco-4-nor-cholestane-5-one-3-methylamide are recovered with a yield of 68%.

Analysis
¹H-NMR (CDCl₃): consistent
Retention time: 4 min 42 hundredths
Detected peaks in mass spectrometry: [M+H]⁺=418; [2M+H]⁺=835

Step B: Next, 50 mg of 3,5-seco-4-nor-cholestane-5-one-3-methylamide, 50 mg of hydroxylamine hydrochloride in 1 mL of pyridine are introduced into a flask. The reaction medium is stirred for 16 hours at room temperature and then concentrated under reduced pressure. The obtained residue is taken up in a CH₂Cl₂/H₂O mixture; the organic phase is separated, washed with water, dried on anhydrous magnesium sulfate and concentrated under reduced pressure. 40.6 mg of 3,5-seco-4-nor-cholestane-5-one oxime-3-methylamide are recovered with a yield of 78%.

Analysis
¹H-NMR (CDCl₃): consistent
Retention time: 3 min 70 hundredths
Detected peaks in mass spectrometry: [M+H]⁺=433; [2M+H]⁺=865

Example 2

Synthesis of
3,5-seco-4-nor-cholestane-5-one-3-dimethyl alcohol

Step A: In a flask, 10.5 g of 3,5-seco-4-nor-cholestane-5-one-3-oic acid are solubilized in 378 mL of methanol and 146 mL of dichloromethane. The mixture is cooled to 0° C. and 5.7 mL of thionyl chloride are added dropwise. It is then stirred for 2 hours at room temperature. The reaction medium is concentrated under reduced pressure, co-evaporated with toluene and then with dichloromethane. 10.3 g of 3,5-seco-4-nor-cholestane-5-one-3-methyl ester are obtained with a yield of 94%. The product is used as such without any purification.

¹H-NMR (CDCl₃): consistent
Retention time: 4 min 69 hundredths
Detected peak in mass spectrometry: {M+H}⁺=419; [2M+H]⁺=785

Step B: In a flask, 9.62 g of 3,5-seco-4-nor-cholestane-5-one-3-methyl ester is put into a solution of 25 mL of trimethyl orthoformate and 53 mL of ethylene glycol. 400 mg (2.3 mmol) of anhydrous p-toluene sulfonic acid are added and then stirred overnight at room temperature. Ethyl acetate is added to the reaction medium; washing is performed with a 10% sodium acid carbonate solution. The organic phase is separated, dried on anhydrous magnesium sulphate and concentrated under reduced pressure. 9.95 g of 3,5-seco-4-nor-cholestane-5,5-(ethylene dioxy)-3-methyl ester were obtained with a yield of 93%. The product is used as such without any purification.

¹H-NMR (CDCl₃): consistent
Retention time: 5 min 76 hundredths
Detected peak in mass spectrometry: {M+H}⁺=463

Step C: In a flask, 300 mg of 3,5-seco-4-nor-cholestane-5,5-(ethylene dioxy)-3-methyl ester are solubilized in 5 mL of anhydrous THF. The medium is cooled down to −45° C. and 1.36 mL of a 1.6M methyl lithium solution in ether are then added dropwise. After 30 minutes of stirring at −45° C., a few drops of methanol are added to the reaction medium and the latter is brought back to room temperature. 20 mL of diethyl ether is taken up and washed with a solution saturated with sodium bicarbonate, and then with a solution saturated with sodium chloride. The organic phase is dried on magnesium sulphate, and then concentrated under reduced pressure. 295 mg of 3,5-seco-4-nor-cholestane-5,5(ethylene dioxy)-3-dimethyl alcohol (MW=462) are obtained with a yield of 98%.

Retention time: 5 min 56 hundredths
Detected peaks in mass spectrometry: [M⁻(CH₂OH—CH₂OH+H₂O)+H]⁺=401

Step D: In a flask, 6 mL of a water/acetic acid (1/1) mixture and 295 mg of 3,5-seco-4-nor-cholestane-5,5(ethylene dioxy)-3-dimethyl alcohol are added; and refluxed for 1h30. After cooling, the reaction medium is diluted with ethyl acetate, washed with a solution saturated with sodium chloride, and then with a solution saturated with sodium bicarbonate. Finally, the organic phase is dried on magnesium sulfate and concentrated under reduced pressure. The obtained raw product is purified by flash chromatography (petroleum ether/ethyl acetate (8/2)). 180 mg of 3,5-seco-4-nor-cholestane-5-one-3-dimethyl alcohol are obtained with a yield of 68%.

¹H-NMR (CDCl₃): consistent
Retention time: 5 min 08 hundredths
Detected peaks in mass spectrometry: [M+H]⁺=419; [M—H₂O+H]⁺=401; [2M+H]⁺=837

Example 3

Synthesis of 3,5-seco-4-nor-cholestane-5-one
oxime-3-dimethyl alcohol 1 g of the compound of Example 2, 1 g of hydroxylamine hydrochloride in 53 mL of pyridine and a few mL of dichloromethane for solubilizing the ketone, are introduced into a flask. The reaction medium is stirred for 16 hours at room temperature and then concentrated under reduced pressure. The obtained residue is taken up in a CH₂Cl₂/H₂O mixture; the organic phase is separated, washed with water, dried on anhydrous sodium sulphate and concentrated under reduced pressure. 814 mg of 3,5-seco-4-nor-cholestane-5-one oxime-3-dimethyl alcohol are recovered with a yield of 78%.

¹H-NMR (CDCl₃): consistent
Retention time: 5 min 09 hundredths
Detected peaks in mass spectrometry: [M+H]⁺=434; [2M+H]⁺=867

Example 4

Synthesis of 3,5-seco-4-nor-cholestane-5-one
oxime-3-methyl alcohol

Step A: 2 g of 3,5-seco-4-nor-cholestane-5,5(ethylene dioxy)-3-methyl ester in 26 mL of dioxane are placed in a flask. 8.6 mL of a 1N soda solution are added. The reaction medium is refluxed for 1 h 30 and dioxane is evaporated under reduced pressure. The obtained solution is acidified by adding a 1N hydrochloric acid solution right up to pH=1 and is extracted twice with toluene. The organic phases are collected, dried on anhydrous magnesium sulphate and concentrated under reduced pressure. 1.92 g of 3,5-seco-4-nor-cholestane-5,5(ethylene dioxy)-3-oic acid are recovered with a yield of 99%, and used without any additional treatments in the following step.

Step B: 1.9 g of 3,5-seco-4-nor-cholestane-5,5(ethylene dioxy)-3-oic acid in 30 mL of dichloromethane are placed in a flask. To this solution, 1.6 g of EDCI, 743 mg of HOBT, 537 mg of N,O-dimethylhydroxylamine hydrochloride and then 1.37 mL of triethylamine are added dropwise. Stirring is performed at room temperature for 16 hours. A CH₂Cl₂/H₂O mixture is added to the reaction medium and the latter is extracted 3 times with dichloromethane. The organic phases are collected, dried on anhydrous magnesium sulphate and concentrated under reduced pressure. The obtained residue is purified by flash chromatography ($CH_2Cl_2$/ethyl acetate (8/2)). 1.46 g of 3,5-seco-4-nor-cholestane-5,5(ethylene dioxy)-3-(N,N-methoxy-methyl) amide are recovered with a yield of 70%.

$^1$H-NMR ($CDCl_3$): consistent
Retention time: 5 min 31 hundredths
Detected peak in mass spectrometry: $[M+H]^+$=492

Step C, 1.4 g of 3,5-seco-4-nor-cholestane-5,5(ethylene dioxy)-3-(N,N-methoxy-methyl) amide in 20 mL of anhydrous tetrahydrofurane are introduced into a flask under argon and are cooled to 0° C. 3.38 mL of a 1.6M methyl lithium solution in ether is then added dropwise. The reaction medium is stirred for 3 h 40 at 0° C. and then a solution of 0.72 mL of concentrated hydrochloric acid in 7.28 mL of water are then added dropwise. The tetrahydrofurane is evaporated under reduced pressure; the obtained aqueous solution is basified by adding 1N soda right up to pH=10. It is extracted with diethyl ether; the organic phases are collected, dried on anhydrous magnesium sulphate and concentrated under reduced pressure. The obtained residue is purified by flash chromatography (petroleum ether/ethyl acetate (9/1)). 930 mg of 3,5-seco-4-nor-cholestane-5,5(ethylene dioxy)-3-methyl ketone are recovered with a yield of 73%.

$^1$H-NMR ($CDCl_3$): consistent
Retention time: 5 min 65 hundredths
Detected peak in mass spectrometry: $[M+H]^+$=403

Step D: 119 mg of 3,5-seco-4-nor-cholestane-5,5(ethylene dioxy)-3-methyl ketone of step C in 1.5 mL of methanol are placed in a flask. The mixture is cooled to 0° C. and 10 mg of sodium borohydride are added. The reaction medium is stirred for 1 h at 0° C. and then concentrated under reduced pressure, The residue is taken up in water and extracted with dichloromethane. The organic phase is dried on magnesium sulphate and concentrated under reduced pressure. 94 mg of 3,5-seco-4-nor-cholestane-5,5(ethylene dioxy)-3-methyl alcohol are recovered with a yield of 78%, this product is used as such.

$^1$H NMR ($CDCl_3$): consistent
Retention time: 5 min 22 hundredths
Detected peaks in mass spectrometry: $[M+H]^+$=387

Step E: The operation is carried out as in step D of Example 2 for de-protecting the ketone in 5.

Step F: 121 mg of 3,5-seco-4-nor-cholestane-5-one-3-methyl alcohol, 1.5 mL of pyridine and 121 mg of hydroxylamine hydrochloride are introduced into a flask. The solution is stirred for two days at room temperature. The reaction medium is concentrated under reduced pressure, taken up in water and extracted with dichloromethane. The organic phase is then washed with water, and then dried on magnesium sulphate and concentrated under reduced pressure. The thereby obtained product is purified by flash chromatography (petroleum ether/ethyl acetate (9/1)). 66 mg of 3,5-seco-4-nor-cholestane-5-one oxime-3-methyl alcohol are obtained with a yield of 53%.

$^1$H-NMR ($CDCl_3$): consistent
Retention time: 4 min 91 hundredths
Detected peaks in mass spectrometry: $[M+H]^+$=420

Example 5

Synthesis of 3,5-seco-4-nor-cholestane-5-one oxime-3-methylamine

Step A: 615 mg of $LiAlH_4$ are suspended in 57 mL of THF in a flask. The suspension is cooled to 0° C. and a solution of 3.0 g of 3,5-seco-4-nor-cholestane-5,5(ethylene dioxy)-3-methyl ester in 57 mL of tetrahydrofurane are added dropwise. Stirring is then performed at 0° C. for 5 hrs. Hydrolysis is performed with precaution by adding a sodium sulphate solution; the obtained white solution is stirred for 30 minutes and then filtered. The filtrate is concentrated under reduced pressure and taken up in water, extracted with ethyl acetate. The organic phase is dried on magnesium sulphate and then concentrated under reduced pressure. 2.55 g of 3,5-seco-4-nor-cholestane-5,5(ethylene dioxy)-3-ol are obtained with a yield of 85%, the product is used as such.

$^1$H-NMR ($CDCl_3$): consistent
Retention time: 4 min 82 hundredths
Detected peaks in mass spectrometry: $[M-(CH_2OH—CH_2OH+H_2O)+H]^+$=373

Step B: In a flask under argon, 476 mg of 3,5-seco-4-nor-cholestane-5,5(ethylene dioxy)-3-ol, are solubilized in 7 mL of dichloromethane, and then 189 mg of neutral alumina and 399 mg of pyridinium chlorochromate are added; stirring is performed at room temperature for 3 h 30. The reaction medium is filtered on Celite®; the filtrate is concentrated under reduced pressure. The obtained residue is purified by flash chromatography (toluene/ethyl acetate 9/1 and then 8/2). 328 mg of 3,5-seco-4-nor-cholestane-5,5(ethylene dioxy)-3-al are obtained with a yield of 69%.

Retention time: 5 min 57 hundredths
Detected peaks in mass spectrometry: $[M+H]^+$=433

Step C: In a flask under argon, 323 mg of 3,5-seco-4-nor-cholestane-5,5(ethylene dioxy)-3-al are solubilized in 3 mL of ethanol, and then 209 µL of triethylamine, 100 mg of methylamine hydrochloride and 444 µL of titanium tetraisopropoxide are added. The reaction medium is stirred for 6 hrs at room temperature, and then 42.5 mg of sodium borohydride are added. Stirring is performed for 16 hours at room temperature. The reaction medium is filtered and washed with dichloromethane, The filtrate is dried on magnesium sulphate and concentrated under reduced pressure. The obtained residue is purified by flash chromatography (dichloromethane/methanol 9/1 to 5/5). 84 mg of 3,5-seco-4-nor-cholestane-5,5(ethylene dioxy)-oxime-3-methylamine are obtained with a yield of 25%.

$^1$H-NMR ($CDCl_3$): consistent
Retention time: 3 min 93 hundredths
Detected peaks in mass spectrometry: $[M+H]^+$=448

Step D: 50 mg of 3,5-seco-4-nor-cholestane-5,5(ethylene dioxy)-3-methylamine and 976 µL of a water/acetic acid 1/1 mixture are added into a flask. The mixture is refluxed for 6 hrs. After cooling, the reaction medium is diluted with ethyl acetate and washed with a solution saturated with sodium chloride and then with a 5% sodium bicarbonate solution. The organic phase is dried on magnesium sulfate and concentrated under reduced pressure. The obtained product is purified by flash chromatography (dichloromethane/methanol (95/5)); 5 mg of 3,5-seco-4-nor-cholestane-5-one-3-methylamine are obtained with a yield of 11%.

$^1$H-NMR ($CDCl_3$): consistent
Retention time: 3 min 68 hundredths
Detected peaks in mass spectrometry: $[M+H]^+$=404

Step E: 5 mg of 3,5-seco-4-nor-cholestane-5-one-3-methylamine, 5 mg of hydroxylamine hydrochloride and 287 µL of pyridine are introduced into a flask. The mixture is stirred for 16 hours at room temperature. It is then taken up in dichloromethane and washed with water. The organic phase is dried on magnesium sulfate and concentrated under reduced pressure. 5 mg of 3,5-seco-4-nor-cholestane-5-one oxime-3-methylamine are obtained with a yield of 91%.

Retention time: 3 min 66 hundredths
Detected peaks in mass spectrometry: [M+H]$^+$=419

Example 6

Synthesis of 3,5-seco-4-nor-cholestane-5-one methyloxime-3-ol 20 mg of 3,5-seco-4-nor-cholestane-5-one-3-ol, 20 mg of O-methyl-hydroxylamine hydrochloride in 1 mL of pyridine are introduced into a flask. Stirring is performed for 36 hrs at room temperature and 10 mg of O-methyl-hydroxylamine hydrochloride are again added. Stirring is again performed for 16 hours at room temperature and the reaction medium is then concentrated under reduced pressure. The obtained residue is taken up in a $CH_2Cl_2/H_2O$ mixture; the organic phase is separated, washed with water, dried on anhydrous magnesium sulphate and concentrated under reduced pressure. 18 mg of a yellow oil which is purified by flash chromatography (petroleum ether/ethyl acetate (9/1)), are obtained. 5.8 mg of 3,5-seco-4-nor-cholestane-5-one methyloxime-3-ol are obtained with a yield of 27%.
Analysis
$^1$H-NMR (CDCl$_3$): consistent
Retention time: 5 min 50 hundredths
Detected peak in mass spectrometry: [M+H]$^+$=420

Example 7

Synthesis of 3,5-seco-4-nor-cholestane-5-one carboxymethyloxime-3-ol 52 mg of ketone, 25 mg of carboxymethoxylamine hemihydrochloride in 0.5 mL of pyridine are introduced into a flask. Stirring is performed for 2 days at room temperature and the reaction mixture is then concentrated under reduced pressure. The obtained residue is taken up in a $CH_2Cl_2/H_2O$ mixture; the organic phase is separated, washed with water and then with a 2% hydrochloric acid solution, dried on anhydrous sodium sulfate and concentrated under reduced pressure. The obtained residue is purified by flash chromatography (petroleum ether/ethyl acetate (8/2)). 24 mg are obtained with a yield of 39% from carboxymethyloxime.
Analysis
$^1$H-NMR (CDCl$_3$): consistent
Retention time: 4 min 40 hundredths
Detected peak in mass spectrometry: [M+H]$^+$=464; [2M+H]$^+$=927

Example 8

A suspension is prepared, fitting the formula 3,5-seco-4-nor-cholestan-5-one oxime-3-ol 20 mg per ml
Excipient: Oily emulsion

Example 9

A dry form is prepared, fitting the formula 3,5-seco-4-nor-cholestan-5-one oxime-3-N,N-dimethyl oxime-3-N,N-dimethylglycine ester hydrochloride 250 mg
Excipient: qsp a gelatine capsule finished to 750 mg

Example 10

Synthesis of 3,5-seco-4-nor-cholestan-5-one oxime-3-N,N-dimethylglycine ester: prodrug of 3,5-seco-4-nor-cholestan-5-one oxime-3-ol 509 mg of 3,5-seco-4-nor-cholestan-5-one-3-ol, 182 mg of N,N-dimethylglycine hydrochloride, 275 mg of EDCI and 207 mg of DMAP in 10-15 mL of dichloromethane are placed into a flask. Stirring is performed at room temperature for 16 hours. A 5% sodium bicarbonate solution is added to the reaction medium and the latter is extracted with dichloromethane. The organic phases are collected, dried on anhydrous sodium sulphate and concentrated under reduced pressure. The obtained residue is purified by flash chromatography (toluene/ethyl acetate (8/2)). 488 mg are recovered with a yield of 78%.
Analysis
$^1$H-NMR (CDCl$_3$): consistent
Retention time: 3 min 77 hundredths
Detected peak in mass spectrometry: [M+H]$^+$=476
The product is then engaged into the following reaction:
488 mg of the obtained product and 488 mg of hydroxylamine hydrochloride in 23 mL of pyridine are introduced into a flask. Stirring is performed for 16 hours at room temperature and the reaction medium is then taken up in a $CH_2Cl_2/H_2O$ mixture; the organic phase is separated, washed with water, dried on anhydrous sodium sulphate and concentrated under reduced pressure. 378 mg of the oxime are recovered with a yield of 75%. The product is then salified in the presence of an ether solution acidified by an HCl solution, in order to obtain the product as a hydrochloride.
Analysis
$^1$H-NMR (CDCl$_3$): consistent
Retention time: 3 min 43 hundredths
Detected peak in mass spectrometry: [M+H]$^+$=491

Example 11

Synthesis of 3,5-seco-4-nor-cholestan-5-one oxime-3-(4-methyl-1-piperazine) propanoate ester: Prodrug of 3,5-seco-4-nor-cholestan-5-one oxime-3-ol 264 mg of 3,5-seco-4-nor-cholestan-5-one-3-ol, 121 mg of 4-methyl-1-piperazine-propanoic acid as a lithium salt, 14.25 mg of EDCI and 106 mg of DMAP in 2 to 3 mL of dichloromethane are placed in a flask. Stirring is performed at room temperature overnight. Water is added to the reaction medium and the medium is extracted with dichloromethane. The organic phases are collected, dried on anhydrous sodium sulfate and concentrated under reduced pressure. The obtained residue is purified by flash chromatography (toluene/ethyl acetate (98/2)). 54 mg of the desired product are recovered with a yield of 15%.
Analysis
$^1$H-NMR (CDCl$_3$): consistent
Retention time: 3 min 66 hundredths
Detected peak in mass spectrometry: [M+H]$^+$=545
The product is then engaged into the following reaction:
30 mg of the obtained product and 30 mg of hydroxylamine hydrochloride in 1.2 mL of pyridine are introduced into a flask. Stirring is performed for 5 h 30 at room temperature and the reaction medium is then taken up in a $CH_2Cl_2/H_2O$ mixture; the organic phase is separated, washed with water, dried on anhydrous sodium sulphate and concentrated under reduced pressure. 19 mg of the oxime are recovered with a yield of 13%.
Analysis
$^1$H-NMR (CDCl$_3$): consistent
Retention time: 3 min 62 hundredths
Detected peak in mass spectrometry: [M+H]$^+$=560
The product is then salified in the presence of an ether solution acidified by an aqueous solution of hydrochoric acid in order to obtain the product as a dihydrochloride.

Example 12

Anti-Apoptotic Effect of 3,5-seco-4-nor-cholestan-5-one oxime-3-ol: Contractility and Apoptosis of Rabbit Ventricular Cardiomyocytes Anti-apoptotic properties of 3,5-seco-4-nor-cholestan-5-one oxime-3-ol (Azasteroidal alkaloids. Synthesis of A-nor-B-homo-5-azacholestane. Rodewald, W. J.; Wicha, J. Univ. Warsaw, Bulletin of the Polish Science Academy, Chemical Science Series (1963), 11(8), pp. 437-441) were analyzed on cardiomyocytes, by a contractile dysfunction test induced by doxorubicin.

Materials et Methods

Compound to be Tested

A stock solution of 3,5-seco-4-nor-cholestan-5-one oxime-3-ol at a concentration of 10 mM in 100% DMSO was used.

The final concentration in DMSO was the same for all the experimental points, independently of the molecular concentrations used.

3,5-seco-4-nor-cholestan-5-one oxime-3-ol was tested at concentrations of 0.1 and 0.3 µM, diluted in a Tyrode solution (composition in mmol/L: NaCl 135, KCl 5.4, $NaH_2PO_4$ 0.33, $CaCl_2$ 1.2, $MgCl_2$ 1.0, Hepes 10; pH adjusted to 7.4 with NaOH).

Obtaining Isolated Cells of Rabbit Ventricular Cardiomyocytes

Isolated ventricular cells are obtained from hearts of male New Zealand rabbits as described in A. d'Anglemont de Tassigny et al., Fund. Clin. Pharmacol, 18: 531-38, 2004. Briefly, the rabbits (2.0-2.5 kg) are anaesthetized with a pentobarbital solution (50 mg/kg) and they then receive heparin (200 IU/kg). The hearts are excised and immediately perfused, for 10-15 minutes by means of a Langendorff apparatus without recirculation with an oxygenated tyrode (calcium-free) isotonic solution (95%, 2-5% $CO_2$) (in mM: NaCl 135, KCl 5.4, $Na_2PO_4$ 0.33, $MgCl_2$ 1.0, HEPES 10, pH adjusted to 7.4 with 1N NaOH at 37° C., 280-300 mOsmol/$kgH_2O$). Next, all the hearts are perfused for 3 minutes in the "recirculation" mode with the same calcium-free Tyrode solution (coronary flow rate, 10-15 mL/min) added with 1 mg/mL of type II collagenase and 0.28 mg/mL of XIV type protease. Finally, all the hearts are perfused in a mode without any recirculation with the same solution of Tyrode supplemented with 0.3 mM of $CaCl_2$ for 10 min. The left ventricle is removed and cut into small pieces; cell dissociation is achieved by mild mechanical stirring. Extracellular calcium is added by increments every 15 minutes, in order to reach a physiological concentration of 1.0 mM. The isolated myocytes are maintained in a serum-free medium containing (in mM) NaCl 110, KCl 5.4, $Na_2PO_4$ 0.33, $NaHCO_3$ 25, Glucose 5, $MgCl_2$ 0.8, $CaCl_2$ 1, pH adjusted to 7.4, right up to 1 h 30 before experimentation. All the cells are rod-like, have a pale crossed striation and do not have any vesicle at their surface under the optical microscope.

Marking with Annexin V

Annexin V marking of phosphatidylserine was used as a quantitative method for measuring apoptosis by using the MiniMacs cell isolation kit (Miltenyi Biotec, Bergisch, Gladbach, Germany). Briefly, the cells exposing phosphatidylserine are magnetically marked with annexin V microbeads, and then passed into a column placed in a magnetic field. The marked cells (which have magnetically marked phosphatidylserine) are retained in the column whereas those which are not marked (necrotic and no-apoptotic cells) are not retained. The column is removed from the magnetic field, the cells exposing phosphatidylserine, magnetically retained, are eluted as a positive fraction and counted with a Mallassez cell counter. The percentage of apoptotic cells is then referred to the initial number of cells.

Measurement of Caspase-3 Activity

Caspase-3 activity is used as a quantitative method for measuring apoptosis. Briefly, the cells are lysed and the supernatant is used for measuring caspase-3 activity by using the AK-005 kit (Biomol Research Laboratories, Plymouth Meeting, Pa., USA). The fluorogenic substrate for measuring caspase-3 activity (DEVD) is marked with the fluorochrome, 7-amino-4-methyl coumarine (AMC), which produces yellow-green fluorescence detectable in UV light at 360/460 nm for 210 min. AMC is released from the substrate by cleavage by caspase-3, the expression of the enzyme is expressed in fmol/min.

Measurement of Contractility

Myocytes are transferred in a continuously perfused chamber at 37° C., and positioned on the stage of an inverted microscope. The chamber is perfused with physiological buffer containing (en mM): NaCl 140; KCl 5.4; $CaCl_2$ 1; $MgCl_2$ 0.8; HEPES 10 and glucose 5.6 (pH=7.4; 290 mOsmol/$kgH_2O$).

Contraction of the myocytes is induced once a second (1 Hz) with platinum field electrodes placed in the chamber and connected to a stimulator. The images are captured continuously with a ×20 objective and transmitted to a CCD camera at a rate of 240 samples/s. The images of the CCD camera are projected on a video screen.

The myocytes were selected for the study according to the following criterion: a rod-like aspect with very apparent striations and no intracellular vacuola, no spontaneous contraction when they are stimulated with 1 mM $Ca^{2+}$, and with constant rest length and contraction amplitude. The length of the sarcomers was measured by means of a video image analysis program and the data were acquired at a rate of 240 samples/s. The camera images were converted into sarcomer length measurements. The contraction percentage is calculated from these data on the length of the sarcomer.

Data Analysis

All the data were expressed as mean±standard deviation. Comparisons of data between different groups were carried out by ANOVA followed by a Student test with a significant difference at $p<0.05$.

Experimental Procedure

Apoptosis is induced in isolated cardiomyocytes by 3-8 hour exposure to 1 µM of doxorubicin added into an isotonic solution containing (in mM) NaCl 110, KCl 5.4, $Na_2PO_4$ 0.33, $NaHCO_3$ 25, glucose 5, $MgCl_2$ 0.8, $CaCl_2$ 1, pH adjusted to 7.4. Annexin V marking was achieved 3 hours after the beginning of the exposure to doxorubicin since this phenomenon appears very early in the apoptotic cascade. Caspase-3 activity measurements are carried out 8 hrs after exposure to doxorubicin since this phenomenon occurs later in the apoptosis phenomenon. The contractility of cardiomyocytes was measured every hour during the 8 hrs of exposure to doxorubicin. After all the treatments, the cells were compared with control cardiomyocytes not exposed to doxorubicin.

The cardiomyocytes were pre-treated with the 3,5-seco-4-nor-cholestan-5-one oxime-3-ol compound for 15 min before exposure to doxorubicin. Two concentrations of this compound were tested during this study: 0.1 and 0.3 µM.

Results

The mean length of the sarcomers of the cells used in this study was not significantly different among the groups.

Effect of doxorubicin on the contractility of myocytes and apoptosis

Exposure to doxorubicin resulted in a decrease over time of the shortening of the sarcomer. The shortening of the peak under doxorubicin was similar to the control during the first three hours and then became significantly reduced after 4 hrs of exposure (−53.20±7.70% versus −19.49±2.06% relatively to the base line of doxorubicin and of the control, respectively ($p<0.05$, n=5)).

Treatment with 1 μM of doxorubicin induced apoptosis with a significant increase in annexin V marking and in caspase-3 activity.

Effect of 3,5-seco-4-nor-cholestan-5-one oxime-3-ol on dysfunction at a level of contractility induced by doxorubicin and on apoptosis.

Treatment with 1 μM of doxorubicin resulted in a significant reduction of shortening of the ventricular cardiomyocyte peak which is abolished in the presence of 3,5-seco-4-nor-cholestan-5-one oxime-3-ol (0.1 and 0.3 μM). Indeed, after 4 hrs of exposure, the shortening of the peak under doxorubicin (−53.20±7.70%) became significantly reduced with the compound at 0.1 μM (18.9±5.4%) and at 0.3 μM (−8.1±9.6%) relatively to the base line.

Further, annexin V marking and caspase-3 activity increases due to doxorubicin were blocked by 3,5-seco-4-nor-cholestan-5-one oxime-3-ol at 0.1 and 0.3 μM.

Apoptosis evaluated as a % of change in annexin V marking 3 hrs after doxorubicin gave the following results: control: 100%; doxorubicin: 320%±48.7; doxorubicin+0.1 μM 3,5-seco-4-nor-cholestan-5-one oxime-3-ol: 116.3%±15.1; doxorubicin+0.3 μM 3,5-seco-4-nor-cholestan-5-one oxime-3-ol: 137.3%±19.3. The results concerning caspase-3 activity measurements are the following: control: 19±9 fmol/min; doxorubicin: 120±15 fmol/min; doxorubicin+0.1 μM 3,5-seco-4-nor-cholestan-5-one oxime-3-ol: 27±20 fmol/min; doxorubicin+0.3 μM 3,5-seco-4-nor-cholestan-5-one oxime-3-ol: 15±7 fmol/min.

Comments and Conclusions

The 3,5-seco-4-nor-cholestan-5-one oxime-3-ol compound shows a cardioprotective effect on contractility dysfunction induced by doxorubicin and on apoptosis on isolated rabbit cardiomyocytes. The molecule, when it is used at suitable dosages, may actually provide protection against cardiotoxicity induced by doxorubicin which is known to be the limiting factor in the treatment of cancer patients with this anthracyclin. Thus, the 3,5-seco-4-nor-cholestan-5-one oxime-3-ol compound may be used for limiting doxorubicin cardiotoxicity in these patients.

Example 13

Effect of the Compounds, 3,5-seco-4-nor-cholestan-5-one oxime-3-ol and 3,5-seco-4-nor-cholestan-5-one oxime-3-N,N-dimethylglycine ester, in an In Vivo Model of Myocardium Infarction in Mice The purpose of this experiment is to study in vivo the cardioprotective properties of the compounds, 3,5-seco-4-nor-cholestan-5-one oxime-3-ol and 3,5-seco-4-nor-cholestan-5-one oxime-3-N,N-dimethylglycine ester, in a murine coronary occlusion-reperfusion model.

The compounds to be tested are administered intravenously in mice, 5 minutes before reperfusion of the myocardium ischemiated beforehand. As controls, carriers of the compounds beta-cyclodextrin (hereafter called βCD) and water, respectively, are administered under the same conditions as for the compounds.

In order to determine the effect of the tested compounds, the size of the infarction is measured after 24 hour reperfusion.

Surgical Instrumentation for Animals 6-8 week old male C57BL6 mice are anaesthetized with sodium pentobarbital (50 mg/kg i.p.) and are ventilated after intubation with an $O_2/CO_2$ (95%/5%) mixture throughout the experiment. The surface electrocardiogram (ECG) is recorded and viewed on an oscilloscope all along surgery. Under strict asepsis conditions, the jugular vein is catheterized for intravenous administration of the compounds. A left lateral thoracotomy is performed and after pericardiotomy, a major branch of the left coronary artery is localized in the latero-posterior region of the left ventricle. A prolene no. 8 suture is positioned around this artery so as to form a mobile loop for making a temporary coronary occlusion.

Experimental Procedures

All the mice were subject to a 30 minute temporary coronary occlusion. Ischemia of the myocardium region is confirmed by cyanosis of the myocardium surface and a deviation of the ST segment of the electrocardiogram.

Each of the compounds (treated group, n=10) or its solvent (control group, n=10) was administered as a bolus intravenously, 5 min before lifting the 30 minutes of coronary occlusion.

3,5-seco-4-nor-cholestan-5-one oxime-3-ol, dissolved beforehand to a final concentration of 0.46 mg/ml in a 30% βCD solution in phosphate buffer prepared by saturation followed by centrifugation, is administered at a dosage of 1 mg/kg.

3,5-seco-4-nor-cholestan-5-one oxime-3-N,N-dimethylglycine ester, dissolved beforehand to a final concentration of 1.56 mg/ml in sterile water by stirring and sonication, is administered at a dosage of 3.9 mg/kg.

The same volume of carrier is administered in the corresponding control groups.

Reperfusion was confirmed by the aspect of the QRS segment of the electrocardiogram.

After closing the thorax, plane by plane, and evacuating the pneumothorax by suction with a drain, the mice are then gradually woken up and deprived of their ventilatory assistance until they resume normal spontaneous ventilation. If necessary, buprenorphine (1 mg/kg) is administered intraperitoneally in order to provide effective antalgic coverage.

Twenty four hours after the end of coronary occlusion, the mice are re-anaesthetized with sodium pentobarbital (50 mg/kg i.p.) and heparin is administered intravenously (Choay© heparin 1,000 IU/kg). A ligature of the coronary artery is achieved at the same location having been subject to the first occlusion 24 h previously. The mice are then euthanized with a lethal saturated dose of potassium chloride and their heart is rapidly excised and then mounted through the aorta artery on a retrograde perfusion system of the Langendorff type.

A 5% Evans blue solution is perfused retrogradely so that the healthy myocardium is colored in blue; the area made ischemic during the coronary occlusion, or <<area of risk AR>> remaining uncolored by default.

The left ventricle is then cut out into 5 slices with equal thicknesses (1 mm) by means of a slicer specially designed for hearts of mice (Les Isolants de Paris, Palaiseau), which are then weighed.

These slices are incubated in a 1% triphenyltetrazolium chloride solution (TTC, Sigma, Poole, UK) at pH 7.4 for 20 min at 37° C. and then set in 4% formol. TTC has the property of coloring the non-infarcted myocardium in red, and so showing the infarcted areas in white. Each heart slice is placed under a stereo microscope for taking a high definition digital photograph.

Quantification of infarction and the area of risk is carried out by planimetry (Scion Image, Scion, Frederick Md., USA) and referred to the weight of each slice.

The area of risk (non-blue area) is expressed as a percentage of the weight of the left ventricle. The infarction sizes are expressed as a percentage of the weight of the area of risk.

All the infarction size and risk area values are expressed as mean±SEM. A one-factor ANOVA followed by a non-pair Student t test with Bonferonni correction is used for comparing the areas of risk and the infarction sizes between the experimental groups, the significance threshold being set to $p<0.05$.

Results and Conclusions

The infarction sizes of mice treated with the compounds significantly differ from those of mice treated with the carrier.

The results shown in the table below are expressed by the area of risk on the one hand and by the infarction size on the other hand.

| Treated mice | Area of risk | Infarction size |
|---|---|---|
| 3,5-seco-4-nor-cholestan-5-one oxime-3-ol | 9 +/− 4% | 21 +/− 7% |
| Carrier | 14 +/− 4% | 33 +/− 7% |
| | $P < 0.01$ | $P < 0.0007$ |
| Infarction size reduction | | 36.4% |
| 3,5-seco-4-nor-cholestan-5-one oxime- 3-N,N-dimethylglycine ester | 8 +/− 3% | 23 +/− 9% |
| Carrier | 16 +/− 8% | 40 +/− 15% |
| | $P < 0.07$ | $P < 0.006$ |
| Infarction size reduction | | 42.5% |

In the experimental model used, both tested compounds reduce the infarction size. Further the results have shown that the compounds reduce the infarction sizes regardless of the extension of the area of risk.

These results therefore show that both of these compounds have cardioprotective effects in vivo.

Example 14

Effect of the Compound, 3,5-seco-4-nor-cholestan-5-one oxime-3-ol, in an In Vivo Model of Acute Hepatotoxicity In this experiment, the 3,5-seco-4-nor-cholestan-5-one oxime-3-ol compound's capability of protecting hepatocytes is tested.

Hepatocytes like many other cells bear the Fas/CD95 receptor on their cytoplasmic membrane. Stimulation of this Fas route induces cell death by activating the caspase cascade.

An acute model of hepatic damage may be induced by a single injection of the Jo2 anti-Fas antibody (Ogasawara et al., Nature, August 1993), producing severe hepatic damages and resembling viral, auto-immune or drug-induced hepatitis.

Alanine Aminotransferase (ALAT) also called Serum Glutamic Pyruvic Transaminase (SGPT) is an enzyme present in hepatocytes. Its activity significantly increases in plasma after hepatic lysis and is therefore a good marker for evaluating hepatic damage.

Materials and Methods

Animals

Male adult CD1 mice from the breeder "Elevage Janvier", (Le Genest-Saint-Isle, France) were used. The animals were identified individually and had free access to water and food.

The installations were maintained with a light control cycle (7:00 am-7:00 pm), and at temperatures of 20±2° C. with 50±20% humidity.

Preparation of the Jo2 Antibody

A stock solution of monoclonal hamster anti-mouse CD95 (Fas) antibody, called Jo2, from Pharmingen (BD Biosciences, ref. 554254 batch 32699) is prepared at a concentration of 1 mg/mL in water. The dilutions used are made in 0.9% sodium chloride in water.

Preparation of the Compound to be Tested

The desired amount of 3,5-seco-4-nor-cholestan-5-one oxime-3-ol is weighed and milled into a fine powder, and then mixed with Cremophore EL (Sigma C5135) and absolute ethanol (Carlo Erba RPE 41571) (5% and 10% of the final volume, respectively). After complete dissolution, 0.9% sodium chloride in water is added extemporaneously (85% of the final volume).

Two types of experiments are conducted: intoxication by Jo2 followed by assaying ALATs and lethal intoxication by Jo2.

—Intoxication by Jo2 and Assaying ALATs:

Procedure

Pretreatment with 3,5-seco-4-nor-cholestan-5-one oxime-3-ol is carried out with dosages of 10 and 30 mg/kg by intraperitoneal administration 1 hr before administering the Jo2 antibody. The Jo2 antibody is administered by injecting intraperitoneally a dose of 125 µg/kg in a volume of 5 mL/kg of body weight.

A control is obtained with animals receiving pretreatment by intraperitoneal administration, 1 hr before administering the antibody, of an identical volume of solution having been used for preparing the compound to be tested, without the compound.

Assaying ALATs

Blood is taken from anaesthetized mice, 24 hrs after administering Jo2. An ALAT assay is conducted by using a kit (Roche Diagnostics) with a spectrophotometer (Hitachi Modular), according to the method standardized by the IFCC (International Federation of Clinical Chemistry).

Results and Conclusions

Intraperitoneal administration of Jo2 at 125 µg/kg does not induce any mortality in mice within 24 hrs following the injection.

ALAT activity is significantly reduced by the compound 3,5-seco-4-nor-cholestan-5-one oxime-3-ol at 10 and 30 mg/kg.

TABLE 1

ALAT activity measured 24 hrs after administering Jo2

| Treatment | ALAT activity (U/L) Average +/− SEM (n) |
|---|---|
| Control | 2,860 ± 382 (61) |
| 3,5-seco-4-nor-cholestan-5-one oxime-3-ol (10 mg/kg) | 511 ± 140 (19) ** |
| 3,5-seco-4-nor-cholestan-5-one oxime-3-ol (30 mg/kg) | 533 ± 150 (20) ** |

** $p < 0.01$, ANOVA followed by Dunnett's comparative test carried out relatively to the placebo group With 3,5-seco-4-nor-cholestan-5-one oxime-3-ol administered at 10 and 30 mg/kg, 1 hr before administering Jo2, cell death induced by a sublethal antibody dose may be limited.

ALAT activity, biomarker of hepatic cytolysis in plasma, is significantly lower in mice treated with 3,5-seco-4-nor-cholestan-5-one oxime-3-ol than in untreated control mice.

—Lethal Intoxication by the Jo2 Antibody

In this experiment, the effect of 3,5-seco-4-nor-cholestan-5-one oxime-3-ol on the survival of animals after administering a lethal dose of the Jo2 antibody is evaluated.

Procedure

The Jo2 antibody is administered by intraperitoneal injection at a dose of 200 ou 250 µg/kg in a volume of 5 mL/kg of body weight.

3,5-seco-4-nor-cholestan-5-one oxime-3-ol is tested at 10 and 30 mg/kg, as a pretreatment, 1 hr before administering Jo2 or as a post-treatment, 1 hr after administering Jo2.

A control is obtained with animals receiving pretreatment by intraperitoneal administration, 1 hr before or 1 hr after administering the antibody, of an identical volume of solution having been used for preparing the compound to be tested, without the compound.

Results and Conclusions

TABLE 2

Survival of the animals after 24 hrs

| | Jo2 dose | Group | Mortality (24 hrs)/total number of animals | Survival rate (%) |
|---|---|---|---|---|
| Experiment 1 | 250 µg/kg | Control | 15/20 | 25 |
| | | With 10 mg/kg pretreatment | 7/20 | 65 |
| Experiment 2 | 250 µg/kg | Control | 18/20 | 10 |
| | | With 30 mg/kg pretreatment | 2/20 | 90 |
| Experiment 3 | 250 µg/kg | Control | 18/20 | 10 |
| | | With 10 mg/kg post-treatment | 17/20 | 15 |
| Experiment 4 | 250 µg/kg | Control | 19/20 | 5 |
| | | With 30 mg/kg post-treatment | 13/20 | 35 |
| Experience 5 | 200 µg/kg | Control | 14/20 | 30 |
| | | With 10 mg/kg post-treatment | 8/20 | 60 |
| Experience 6 | 200 µg/kg | Control | 16/20 | 20 |
| | | With 30 mg/kg post-treatment | 8/20 | 60 |

At the administered doses, the Jo2 antibody induces substantial mortality within 24 hrs (70-100% of the animals) in the control group.

Pretreatment and/or post-treatment with 3,5-seco-4-nor-cholestan-5-one oxime-3-ol at the administered doses induces an increase in the survival rate of the animals.

Thus, when a lethal dose of antibody is used (200 or 250 µg/kg), 3,5-seco-4-nor-cholestan-5-one oxime-3-ol, administered at 10 and 30 mg/kg, 1 hr before or after the antibody, increases the survival rate of the mice over 24 hrs.

CONCLUSIONS

With the model of acute hepatotoxicity induced in mice by an anti-Fas (Jo2) antibody, it was possible to demonstrate the hepatoprotective properties of 3,5-seco-4-nor-cholestan-5-one oxime-3-ol.

With these remarkable effects, the use of compounds of formula I may be contemplated in the preparation of a generally cytoprotective drug.

The invention claimed is:

1. A method for providing cytoprotection, comprising administering to a patient in need thereof at least one compound of formula I

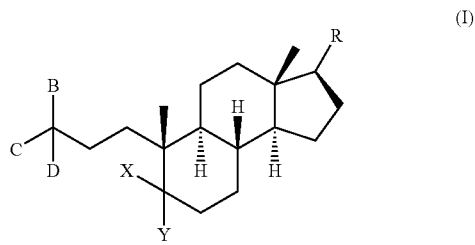

(I)

an addition salt thereof with pharmaceutically acceptable acids, an ester thereof or an addition salt with pharmaceutically acceptable acids of said ester, in a sufficient amount to provide cytoprotection, wherein X and Y taken together represent a ketone function (═O), an oxime group (═NOH) or a methyloxime group (═NHOMe) or X represents a hydroxyl and Y a hydrogen atom;

B represents a hydroxyl radical and C and D, either identical or different, represent a hydrogen atom, or a linear or branched alkyl radical comprising 1 to 4 carbon atoms;

or B and C taken together represent a ketone function and D a methyl, hydroxyl, or methylamine radical, or B and C represent a hydrogen atom and D a methylamine radical, or B and C taken together represent an oxime group and D a methyl radical, and R represents a linear or branched alkyl radical comprising 1 to 10 carbon atoms, or one of its addition salts with pharmaceutically acceptable acids, or one of its esters or one of the addition salts with pharmaceutically acceptable acids of said esters, with the proviso that the cytoprotection is not neuroprotection.

2. The method of claim 1, wherein, in formula I, R represents the cholestane radical of formula II

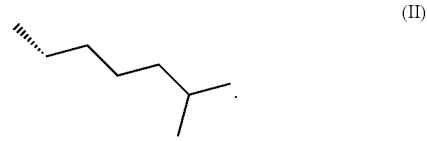

(II)

3. The method of claim 1, wherein, in formula I, X and Y taken together represent a ketone function.

4. The method of claim 1, wherein, in formula I, B represents a hydroxyl radical and C and D, either identical or different, represent a hydrogen atom or a linear or branched alkyl radical comprising from 1 to 4 carbon atoms.

5. The method of claim 1, wherein, in formula I, B and C taken together represent a ketone function and D represents a methyl radical.

6. The method of claim 1, wherein, in formula I, X and Y taken together represent an oxime group.

7. The method of claim 1, wherein the compound of formula I is selected from the group consisting of:

3,5-seco-4-nor-cholestan-5-one oxime-3-ol;

3,5-seco-4-nor-cholestan-5-one oxime-3-methyl alcohol;

3,5-seco-4-nor-cholestan-5-one oxime-3-dimethyl alcohol;
an addition salt thereof with pharmaceutically acceptable acids;
an ester thereof; and
an addition salt with pharmaceutically acceptable acids of said ester.

8. The method of claim 1, wherein the cytoprotection is for protecting cardiac cells.

9. The method of claim 1, wherein the cytoprotection is for protecting hepatic cells.

10. The method of claim 1, wherein the cytoprotection is for protecting cells of a tissue or an organ, before, during or after transplantation.

11. A pharmaceutical composition, comprising at least one compound of formula I

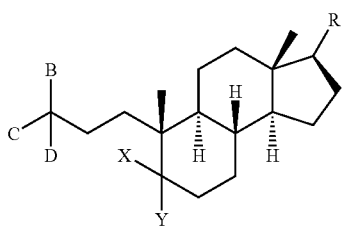

(I)

an addition salt thereof with pharmaceutically acceptable acids, an ester thereof or an addition salt with pharmaceutically acceptable acids of said ester, wherein, in formula I, X and Y taken together represent a ketone function (=O), an oxime group (=NOH) or a methyloxime group (=NHOMe) or X represents a hydroxyl and Y a hydrogen atom;

B represents a hydroxyl radical and C and D, either identical or different, represent a hydrogen atom, or a linear or branched alkyl radical comprising 1 to 4 carbon atoms;

or B and C taken together represent a ketone function and D a methyl, hydroxyl, or methylamine radical, or B and C represent a hydrogen atom and D a methylamine radical, or B and C taken together represent an oxime group and D a methyl radical, and R represents a linear or branched alkyl radical comprising 1 to 10 carbon atoms.

12. The method of claim 1, wherein the cytoprotection provided is against necrosis, and/or pathological apoptosis, and/or necroptosis or a disease selected from the group consisting of diseases of the bones, joints, connective tissue and cartilage, muscular diseases,
skin diseases,
cardiovascular diseases,
circulatory diseases,
hematological and vascular diseases,
diseases of the lung,
diseases of the gastro-intestinal tract,
diseases of the liver,
diseases of the pancreas,
metabolic diseases,
diseases of the kidneys,
viral and bacterial infections
severe intoxications,
degenerative diseases associated with the Acquired Immune
Deficiency Syndrome (AIDS),
disorders associated with aging,
inflammatory diseases,
auto-immune diseases,
dental disorders,
ophthalmic diseases or disorders,
diseases of the audition tracts, and
diseases associated with mitochondria.

13. The method of claim 1, wherein the cytoprotection provided is against diseases associated with mitochondria.

* * * * *